United States Patent [19]

Hjertén et al.

[11] Patent Number: 5,464,517
[45] Date of Patent: Nov. 7, 1995

[54] ELECTROPHORESIS IN LOW CONDUCTIVITY BUFFERS

[75] Inventors: Stellan Hjertén; Jia-Li Liao, both of Uppsala, Sweden

[73] Assignee: Bio-Rad Laboratories, Hercules, Calif.

[21] Appl. No.: 380,425

[22] Filed: Jan. 30, 1995

[51] Int. Cl.⁶ .................... G01N 27/26; G01N 27/447
[52] U.S. Cl. .................... 204/183.2; 204/180.1; 204/182.8; 204/182.9
[58] Field of Search .................... 204/299 R, 180.1, 204/182.8, 182.9, 183.2

[56] References Cited

U.S. PATENT DOCUMENTS 4,936,963  6/1990  Mandecki et al. .................... 204/182.8

OTHER PUBLICATIONS

J. R. Fullarton and A. J. Kenny, "A Rapid System for Preparative Electrophoresis Depending on Isoelectric Buffers of Low Conductivity" The Biochemical Journal 166 (1970) 147–149.

Hjertén, Stellan, "Zone Broadening in Electrophoresis With Special Reference to High–Performance Electrophoresis in Capillaries: An Interplay Between Theory and Practice," Electrophoresis, 1990, pp. 665–690.

*Primary Examiner*—John Niebling
*Assistant Examiner*—John S. Starsiak, Jr.
*Attorney, Agent, or Firm*—Townsend and Townsend and Crew

[57] ABSTRACT

Electrophoresis is performed in buffers which exhibit both substantial buffering capacity and low electrical conductivity, permitting the separations to be performed at high field strengths without loss of resolution. Four classes of buffering agents are cited as examples:

(1) buffering agents with a small number of charged groups per molecule;
(2) carrier ampholytes fractionated to a narrow isoelectric point range;
(3) low molecular weight buffering ampholytes with an isoelectric point which is close in value to one of the pK values of the ampholyte; and
(4) high molecular weight buffering ampholytes in which the acidic and basic groups have the same or very close pK values.

These buffering agents are of particular interest in capillary electrophoresis.

26 Claims, 8 Drawing Sheets

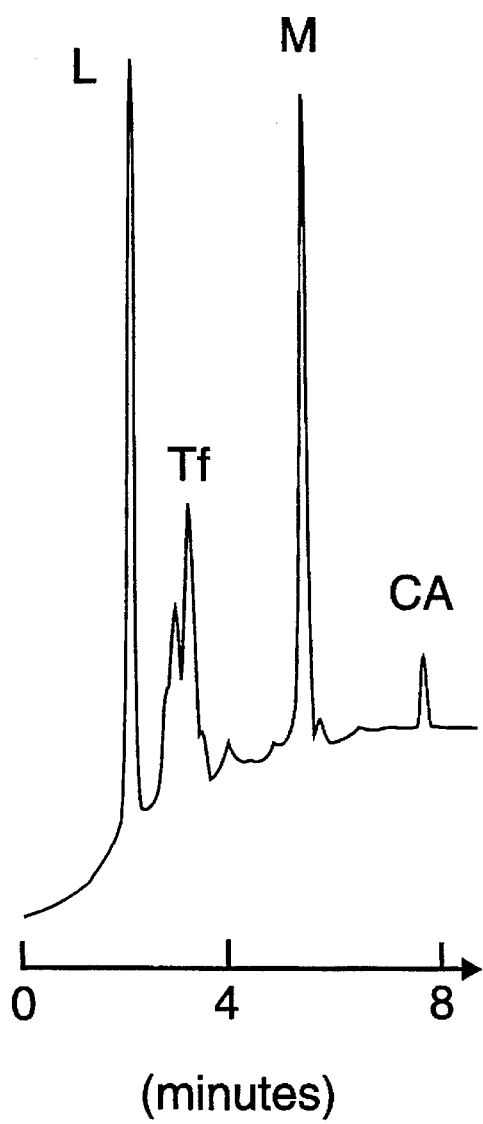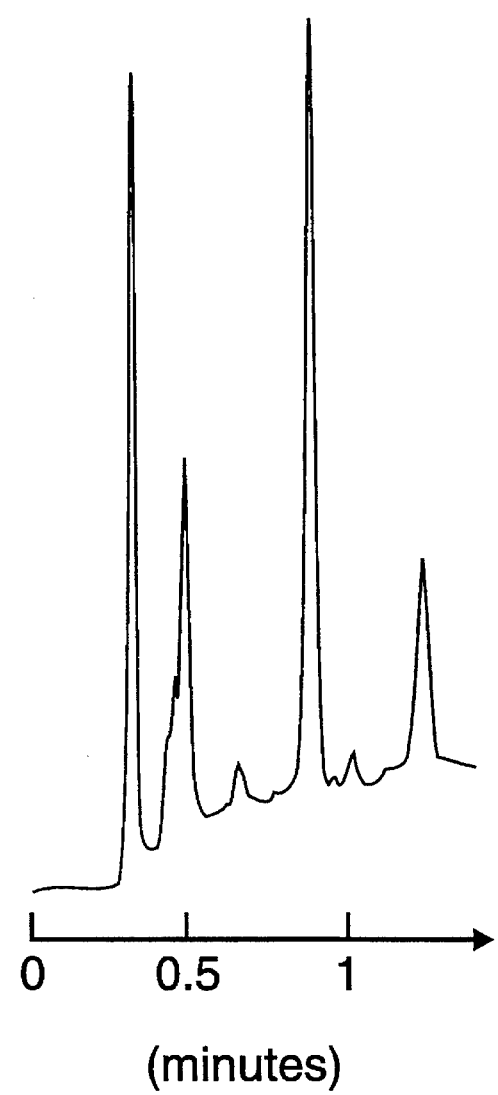
Fig. 4a
Fig. 4b

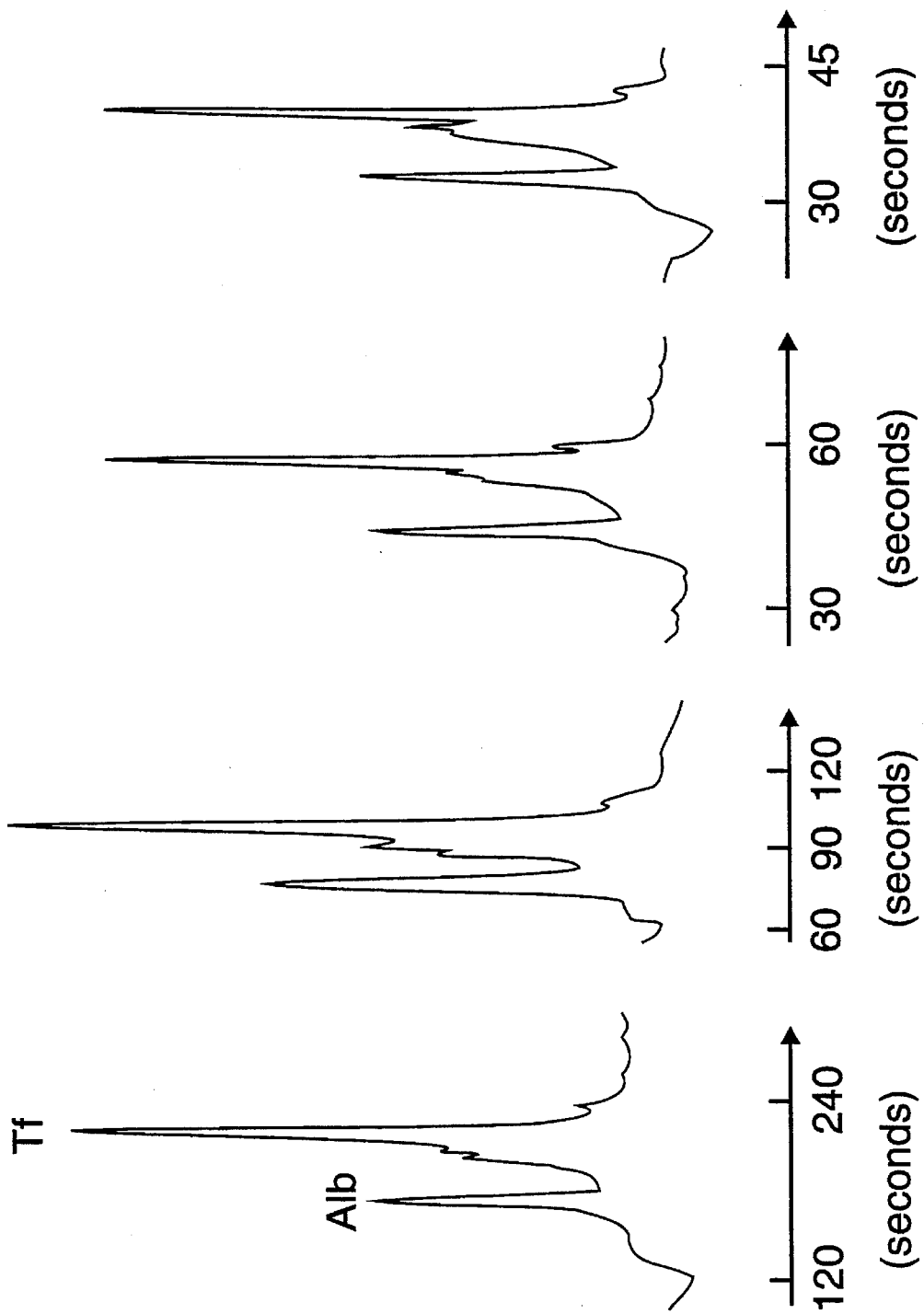

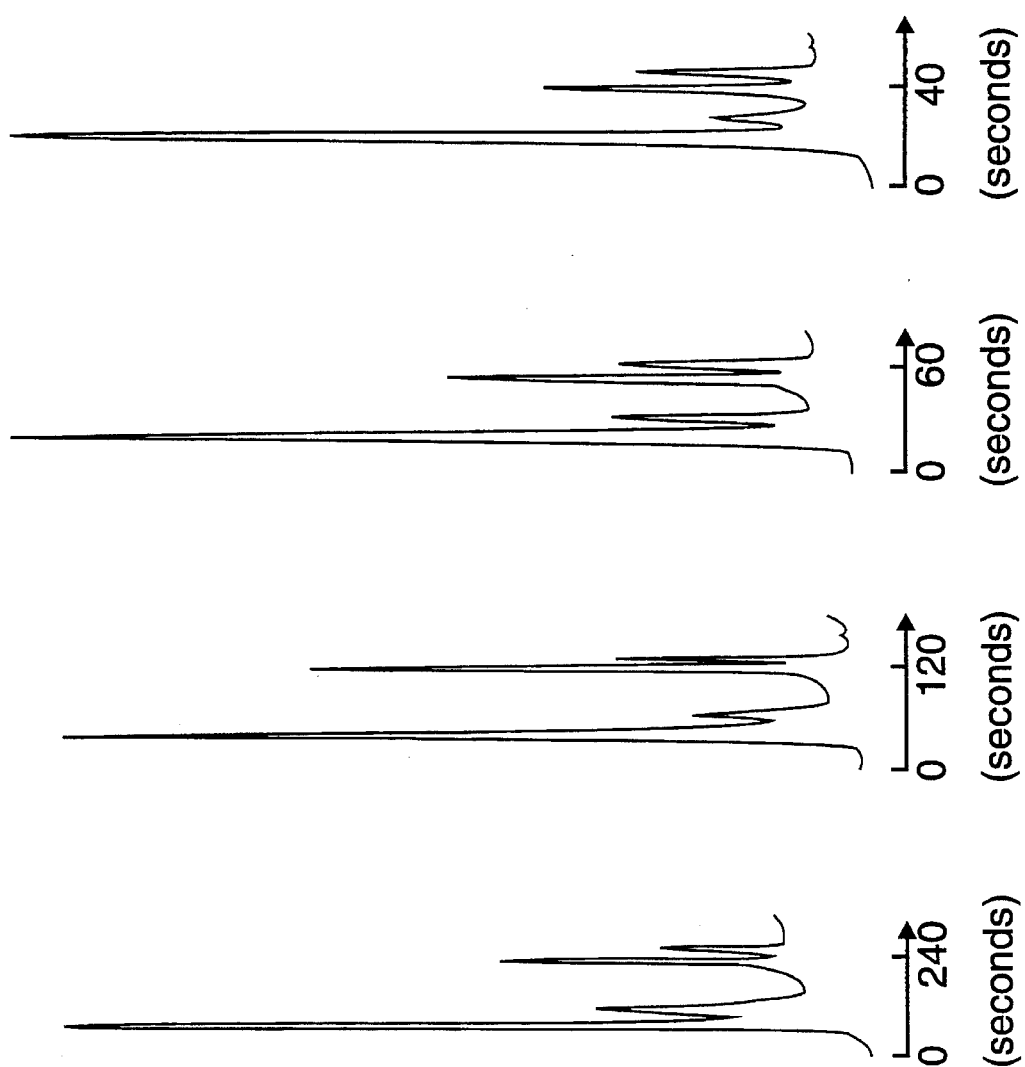

ELECTROPHORESIS IN LOW CONDUCTIVITY BUFFERS

BACKGROUND OF THE INVENTION

Chemical and biochemical analyses are performed in large numbers in chemical, pharmaceutical and clinical laboratories, and technicians in these laboratories see an ever increasing need to shorten the time required for a given analysis. Some of the reasons relate to the cost of labor and the need for the availability of valuable laboratory space and equipment. Other reasons arise from the fact that many substances studied in these analyses are labile, such as substances taking part in fast chemical reactions, including biochemical coupling reactions, and others such as radiolabeled compounds have a short lifetime.

One of the most widely used analytical techniques is electrophoresis, owing to its versatility and its ability to separate and identify the components of complex chemical and biochemical mixtures. The variety of different forms of electrophoresis which are now in use has extended the applicability of the method to analyses of many different types of molecules, ranging from simple organic molecules to macromolecules such as polypeptides, enzymes, blood factors and other biological compounds, and nucleic acids. The development of capillary electrophoresis has further extended the usefulness of the method by permitting analyses to be performed on extremely small samples, and by permitting the electrophoretic media to tolerate high voltages and thereby achieve even shorter separation times and more complex separations. Electrophoresis is commonly performed in capillaries at voltages of 100–300 V/cm without thermally induced zone deformation which can cause a significant loss of resolution. In electrophoresis cells other than capillaries, typical voltages are 10–100 V/cm.

In capillaries as well as in tube gels, slab gels and other configurations of the electrophoresis media, laboratories would benefit from still further decreases in the time required to perform electrophoresis. One logical way to do this would be to increase the rate of migration for individual solutes. The time required for the migration of a solute to a detector is inversely proportional to the field strength, as shown by the following equation:

$$t = \frac{L}{uF} \quad (1)$$

where:
 t is the migration time,
 L is the migration distance to the detector,
 u is the mobility of the solute (i.e., the velocity of the solute divided by the field strength, and
 F is the electrical field strength.

Increasing the field strength would clearly decrease the migration times, but high field strengths are usually accompanied by high Joule heating, which leads to zone deformation and consequently a decrease in solute resolution. High field strengths also cause bubbles of water vapor to form. These bubbles interfere with electrophoretic migration and obscure the resolution of the zones.

SUMMARY OF THE INVENTION

It has now been discovered that electrophoresis can be performed in buffers of low electrical conductivity and yet achieve high resolution. With low conductivity buffers, electrophoresis can be performed at high field strengths while experiencing less of the difficulties encountered with conventional buffers, and one of the discoveries giving rise to this invention is that low conductivity buffers permit one to increase the field strength well beyond levels typically used for capillary electrophoresis without a loss in resolution. This invention is applicable to electrophoresis in general, but is of particular interest in capillary electrophoresis, where the highest field strengths are typically used.

The conductivity $\kappa$ in $ohm^{-1} cm^{-1}$ of a buffer solution in capillary electrophoresis is determined by the following formula:

$$\frac{V}{L'} = \frac{I}{\pi R^2 \kappa}, \text{ or } \kappa = \frac{IL'}{V \pi R^2}$$

where:
 V is the total voltage across the capillary in volts,
 L' is the length of the capillary tube,
 I is the current in amperes, and
 R is the inner radius of the capillary in centimeters.

Equation (2) is cited by Hjertén, S., in "Zone broadening in electrophoresis with special reference to high-performance electrophoresis in capillaries: An interplay between theory and practice", *Electrophoresis* 11:665–690 (1990). Accordingly, this invention resides in the use of buffer solutions having conductivities considerably less than those of buffers of the prior art, whose conductivities in accordance with Equation (2) are in the range of $10^{-3}$ $ohm^{-1}$ $cm^{-1}$ and higher.

The invention further resides in the use of various classes of buffering agents which offer low conductivity while maintaining their effectiveness as buffers. These classes are as follows:

(1) buffering agents with a small number of charged groups per molecule, and preferably of a relatively high molecular weight;

(2) carrier ampholytes fractionated to a narrow pH range by isoelectric focusing;

(3) low molecular weight buffering ampholytes at their isoelectric points, the isoelectric point being one which is close in value to one of the pK values of the ampholyte; and (4) high molecular weight buffering ampholytes in which the acidic and basic groups have the same or very close pK values.

Other features and advantages of the invention will become apparent from the description which follows.

BRIEF DESCRIPTION OF THE DRAWINGS

FIGS. 4*a* and 4*b* are detector traces of electrophoretic separations of a further mixture of macromolecules at two different voltages, using the same buffer as FIGS. 1a and 1b.

FIGS. 6a, 6b, 6c and 6d are detector traces of electrophoretic separations of a mixture of proteins at four different voltages, using a fraction of an isoelectrically focused carrier ampholyte as the buffer.

FIGS. 7a, 7b, 7c and 7d are detector traces of electrophoretic separations of a mixture of proteins at four different voltages, using lysine as the buffer.

DETAILED DESCRIPTION OF THE INVENTION AND PREFERRED EMBODIMENTS

Figures 1A, 1B:
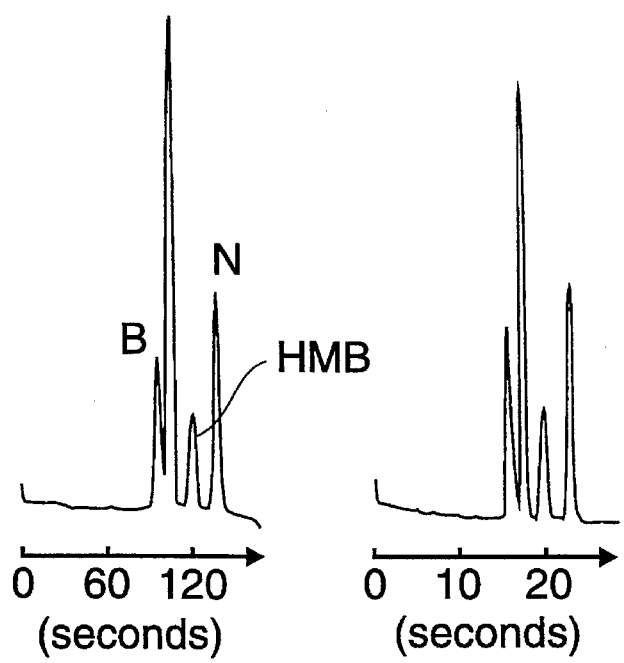
FIGS. 1*a* and 1*b* are detector traces of electrophoretic separations of a mixture of low molecular weight compounds performed at two different voltages. Both separations were performed in a capillary filled with a mixture of polyoxyethylene bis(3-amino-2-hydroxypropyl) and polyoxyethylene bis(acetic acid) as the buffer.
Figures 2A, 2B, 2C, 2D:
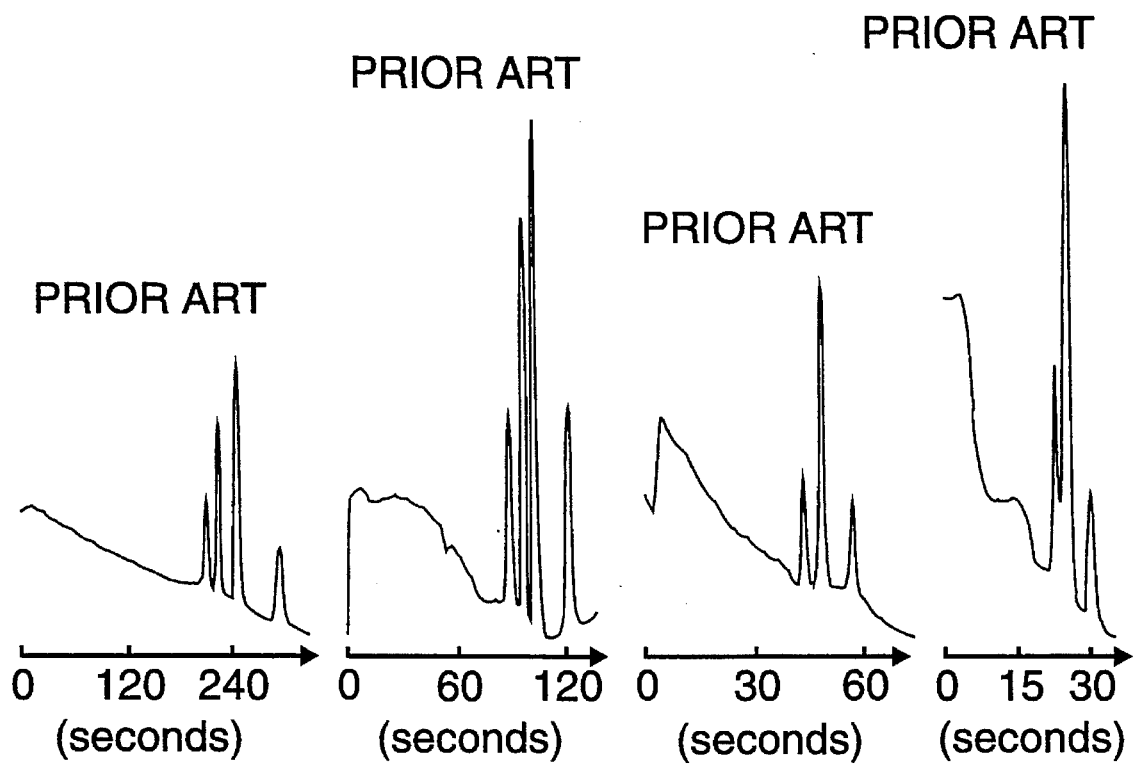
FIGS. 2*a*, 2*b*, 2*c* and 2*d* are detector traces of electrophoretic separations performed with buffers of the prior art, at varying voltages. The sample and capillary were the same as those used in the traces of FIGS. 1*a* and 1*b*.

This invention has applicability to all types of electrophoresis, in cells of all forms and shapes, notably capillaries, slabs, and tubes. In capillaries the separation medium is most often the buffer solution itself, whereas in slab cells, tube cells and gel-filled capillaries, the separation medium is a gel equilibrated and saturated with the buffer solution.

Buffer solutions for use in accordance with this invention are characterized at least in part by a conductivity low enough to permit the use of voltages well in excess of the typical voltages used for capillary electrophoresis, without substantial loss in peak resolution. While the conductivity can vary depending on how fast a separation is desired and therefore how high a voltage is needed, best results in most cases will be obtained with conductivities in the range of $25 \times 10^{-5}$ $ohm^{-1}cm^{-1}$ or less. In preferred embodiments of this invention, the conductivities are within the range of about $1 \times 10^{-5}$ $ohm^{-1}cm^{-1}$ to about $20 \times 10^{-5}$ $ohm^{-1}cm^{-1}$, and in particularly preferred embodiments, the conductivities are within the range of about $2 \times 10^{-5}$ $ohm^{-1}cm^{-1}$ to about $10 \times 10^{-5}$ $ohm^{-1}cm^{-1}$. All such conductivities are as determined by Equation (2) above.

The benefits of this invention are achieved at voltages above the normal range for the particular type of electrophoretic cell. In general, the invention offers benefits at voltages of about 300 volts per cm (along the distance of the direction of the voltage). For capillaries, where the voltages used are generally higher than other forms, preferred voltages for the practice of this invention are in the range of about 600 volts per cm of capillary length or greater. More preferred are voltages of at least about 750 volts per cm of column length, and the most preferred are those of at least about 2,000 volts per cm of column length.

As Equation (2) indicates, the conductivity of the buffer solution for a separation performed in a capillary is readily determined by measuring the current across the capillary. The current in turn is controlled by selection of the buffering agent. Four buffering agents which meet the characteristics of the invention are listed above. Each will now be discussed in detail.

A. Buffering Agents With Few Charged Groups Per Molecule

These buffers achieve a low conductivity by virtue of their small number of charged groups per molecule. The number is preferably in the range of one to four (all ranges in this specification are inclusive of their upper and lower limits), more preferably one to three, and most preferably two. The molecular weights of these agents are preferably about 100 or higher, more preferably about 2,000 or higher, and most preferably about 2,500 to about 5,000. For polymers, these molecular weight ranges refer to weight-averaged molecular weights.

The buffering agents may consist of a single species or a combination of two or more species, to provide both acidic and basic buffering groups. In the case of a mixture of two or more species, the molecular weight ranges cited above refer to the molecular weights which are weight-averaged between the species, as well as within any single species which has an inherent molecular weight range. An example of a buffering agent with a molecular weight below 2,000 is a mixture of diaminopimelic acid with $pK_3$ of 8.8 and 2-amino-2-methyl-1,3-propanediol with pK of 8.4. Examples of buffering agents with molecular weights of about 2,000 and above are derivatized polyoxyethylenes with one to three, and preferably two, charged buffering groups per molecule. The derivatized polyoxyethylenes may be used in combinations, such as for example one containing two basic buffering groups per molecule and a second containing two acidic buffering groups per molecule. One example of such a combination is a mixture of polyoxyethylene bis(3-amino-2-hydroxypropyl) and polyoxyethylene his(acetic acid) with pK values of approximately 9 and 5, respectively.

B. Carrier Ampholytes Isoelectrically Focused and Fractionated to a Narrow pH Range Carrier ampholytes are well known among biochemists who use electrophoresis, and are widely used for isoelectric focusing. The term "carrier ampholyte" refers to a complex mixture of molecules which vary in their isoelectric points. The isoelectric points span a range of values, with a sufficient number of different isoelectric points among the molecules in the mixture to produce essentially a continuum of values of the isoelectric points. Thus, when a cell or vessel such as a flat plate sandwich, a tube, or a capillary is filled with a solution of a carder ampholyte and a voltage is applied across the solution with an acid as the anolyte and a base as the catholyte, the individual ampholyte molecules arrange themselves in order of increasing isoelectric point along the direction of the voltage.

Carder ampholytes can be formed from synthetic substances or from naturally occurring materials. A variety of synthetic carrier ampholytes are available for purchase to laboratories. Examples are the "PHARMALYTES®" of Pharmacia LKB, Uppsala, Sweden, and the "BIO-LYTES®" of Bio-Rad Laboratories, Inc., Hercules, Calif., U.S.A. Examples of carrier ampholytes derived from naturally occurring substances are hydrolyzed proteins of various kinds.

As examples of carder ampholytes, the BIO-LYTES are polyethyleneimines derivatized with acrylic acid, with molecular weights of about 1,000 or greater. The variation in isoelectric point results from the large number of isomeric forms of the starting polyethyleneimine, and the range is achieved in a single derivatization reaction.

For use in the present invention, the carder ampholyte is isoelectrically focused and a fraction at a selected pH is isolated and recovered. The fractionation and recovery are readily performed by preparative isoelectric focusing techniques using laboratory equipment designed for this purpose. An example of a preparative isoelectric focusing cell is the ROTOFOR Cell manufactured by Bio-Rad Laboratories. To achieve the best results, the fractionation is preferably performed in such a manner as to achieve as narrow a pH range as conveniently possible. In preferred embodiments of this aspect of the invention, the pH range of the fraction is at most about 0.2 pH units in width, and in the most preferred embodiments, about 0.1 pH units in width. The midpoint of the pH range in these preferred embodiments is from about pH 3 to about pH 10, and most preferably from about pH 5 to about pH 9.

C. Low Molecular Weight Ampholytes With Multiple pK Values and an Isoelectric Point Close to One pK Value The ampholytes referred to in this section are relatively low molecular weight compounds, preferably with molecular weights of about 1,000 or less, with buffering groups in free form rather than neutralized to salt form. An ampholyte in accordance with this section is dissolved in deionized, carbon-dioxide-free water, and the pH of the resulting solution is very close to the isoelectric point of the ampholyte. The conductivity of the solution is therefore very low. Ampholytes meeting this description which also have a pK value that is approximately equal to the isoelectric point have a substantial buffering capacity sufficient for use as a running buffer for electrophoresis.

Ampholytes of this group preferably have three or more pK values, at least one of which is within about 1.0 of the isoelectric point of the ampholyte. These values can be spaced apart by up to 7 or 8 pK units, or two or more of them can be very close in value. Examples of ampholytes meeting these descriptions are lysine, aspartyl-aspartic acid, glycyl-L-histidine, glycyl-aspartic acid, hydroxylysine, glycyl-glycyl-L-histidine, N-cyclohexyl-iminodiacetic acid, N-(1-carboxycyclohexyD-iminodiacetic acid, and cyclobutane-1,2-bis(N-iminodiacetic acid).

D. High Molecular Weight Ampholytes With Acidic and Basic Groups of Equal pK Value Preferred ampholytes of this type are derivatized polymers having molecular weights of about 2,500 or greater. Polyoxyethylene glycols are examples of polymers which can be used effectively for this purpose. Derivatization can be achieved for example by conjugating the polymer to boric acid or a boric acid derivative at one end and an amino derivative at the other. An example of a boric acid derivative is 3-(aminophenyl) boronic acid; examples of amino derivatives are 2-amino-2-methyl-1,3-propanediol and 2-amino-2-methyl-1-propanol. Substantially equal pK values for the acid and basic groups can be achieved by synthesizing the compound in a manner which will provide the boric acid residue with a pK value which is somewhat higher than that of the amino group residue, then adjusting the pH to the pK value of the amino group by the addition of sorbitol.

The following examples are offered by way of illustration, and are intended neither to limit nor to define the invention in any manner.

EXAMPLES

Materials, Methods and Conditions

The following were obtained from Sigma Chemical Co., St. Louis, Mo., U.S.A.:

2-amino-2-methyl-1,3-propanediol
2,6-diaminopimelic acid
polyoxyethylene bis(acetic acid)
polyoxyethylene bis(3-amino-2-hydroxypropyl)
β-lactoglobulin
equine myoglobin
bovine carbonic anhydrase The following were obtained from Bio-Rad Laboratories, Inc., Hercules, Calif., U.S.A.:

agarose (electrophoresis purity)
acrylamide (electrophoresis purity)
ammonium persulfate (electrophoresis purity)
tetramethylethylenediamine (electrophoresis purity)
protein artion exchange standard consisting of soybean trypsin inhibitor, chicken ovalbumin, conalbumin and equine myoglobin
BIO-LYTE 7-9 (carrier ampholyte for isoelectric focusing)

In addition, γ-methacryloxypropyltrimethylsilane was obtained from Pharmacia LKB, Uppsala, Sweden; human serum albumin and transfer fin from KABI, Stockholm, Sweden; and fused silica tubing from MicroQuartz GmbH, Munich, Germany. Fractionation of BIO-LYTE 7-9 was performed in a ROTOFOR apparatus obtained from Bio-Rad Laboratories, Hercules, Calif., U.S.A.

All electrophoresis experiments were performed in fused silica capillaries coated with linear polyacrylamide to suppress electroendosmosis and adsorption of the solutes to the capillary wall. The capillaries measured 0.05 mm in inside diameter, 0.35 mm in outside diameter, and 15 cm in length, with a migration distance of 11.5 cm to the detector. All samples were predissolved in the buffer to be used in the electrophoresis experiments. Application of the samples to the capillaries was achieved electrophoretically at 1,000 V for 15–20 seconds, and the electrophoretic separations were performed at voltages ranging from 5,000 V to 30,000 V. Detection was performed by absorption of light at 210 nm and at a sensitivity of 0.0005 AUFS (absorbance units full scale), except where noted, on a detector with a short rise time of 0.1 sec. For experiments in a series performed at different voltages, the chart speed was adjusted in proportion to the voltage change to achieve electropherograms of the same width and thereby facilitate comparison among the electropherograms within the series. The time scales in the horizontal axes are modified accordingly, however, so that actual detection times are shown in each electropherogram.

Absorption spectra for Section V below were measured in a 1-cm cuvette in a Model DMS 100/UV Visible Spectrophotometer from Varian Techtron Pty. Limited, Victoria, Australia.

Experiments and Results

I. High Molecular Weight Buffers With Few Charges

A. Polyoxyethylene Bis(3-amino-2-hydroxypropyD and Polyoxyethylene Bis(acetic acid)—FIGS. 1a–4b A series of electrophoretic separations were performed on a mixture of compounds of low molecular weight in a buffer consisting of a mixture of polyoxyethylene bis(3-amino-2-hydroxypropyl) at 0.3 % (weight/volume) and polyoxyethylene bis(acetic acid) at 0.025 % (weight/volume) at pH 8.6. The sample mixture consisted of the following aromatic carboxylic acids:

benzoic acid (B)

4-hydroxybenzoic acid (HB)

4-hydroxy-3-methoxybenzoic acid (HMB)

β-naphthylacetic acid (N)

each dissolved in the buffer to a final concentration of about 0.01 mg/mL. The conductivity of this buffer according to Equation (2) above is $6 \times 10^{-5}$ ohm$^{-1}$cm$^{-1}$. One run was performed at a voltage of 5,000 V (330 V/cm, 0.4 μA). The resulting electropherogram is shown in FIG. 1a, where the peaks are identified by the letter symbols indicated above. A second run was performed at a voltage of 30,000 V (2,000 V/cm, 2.5 μA), and the resulting electropherogram is shown in FIG. 1b.

A comparison between these two electropherograms shows that the buffer used permits analysis at extremely high field strengths, and consequently very short analysis times, without an observable loss of resolution. In addition, the peaks in both electropherograms are symmetrical, indicating that adsorption to the tube wall is negligible and that neither the conductivity nor the pH in a zone differ significantly from those of the surrounding buffer.

For comparison, the same sample was run in a buffer of the prior art at four voltages. The buffer was 0.1M Tris-HCl (tris(hydroxymethyl)aminomethane hydrochloride). The conductivity of this buffer according to Equation (2) above is $120 \times 10^{-5}$ ohm$^{-1}$cm$^{-1}$. The voltages used and the Figures in which the resulting electropherograms appear are as follows:

These four electropherograms show that the strong Joule heat caused a decrease in resolution accompanied by increasing instability in the baseline as the voltage increased.

Figures 3A, 3B:
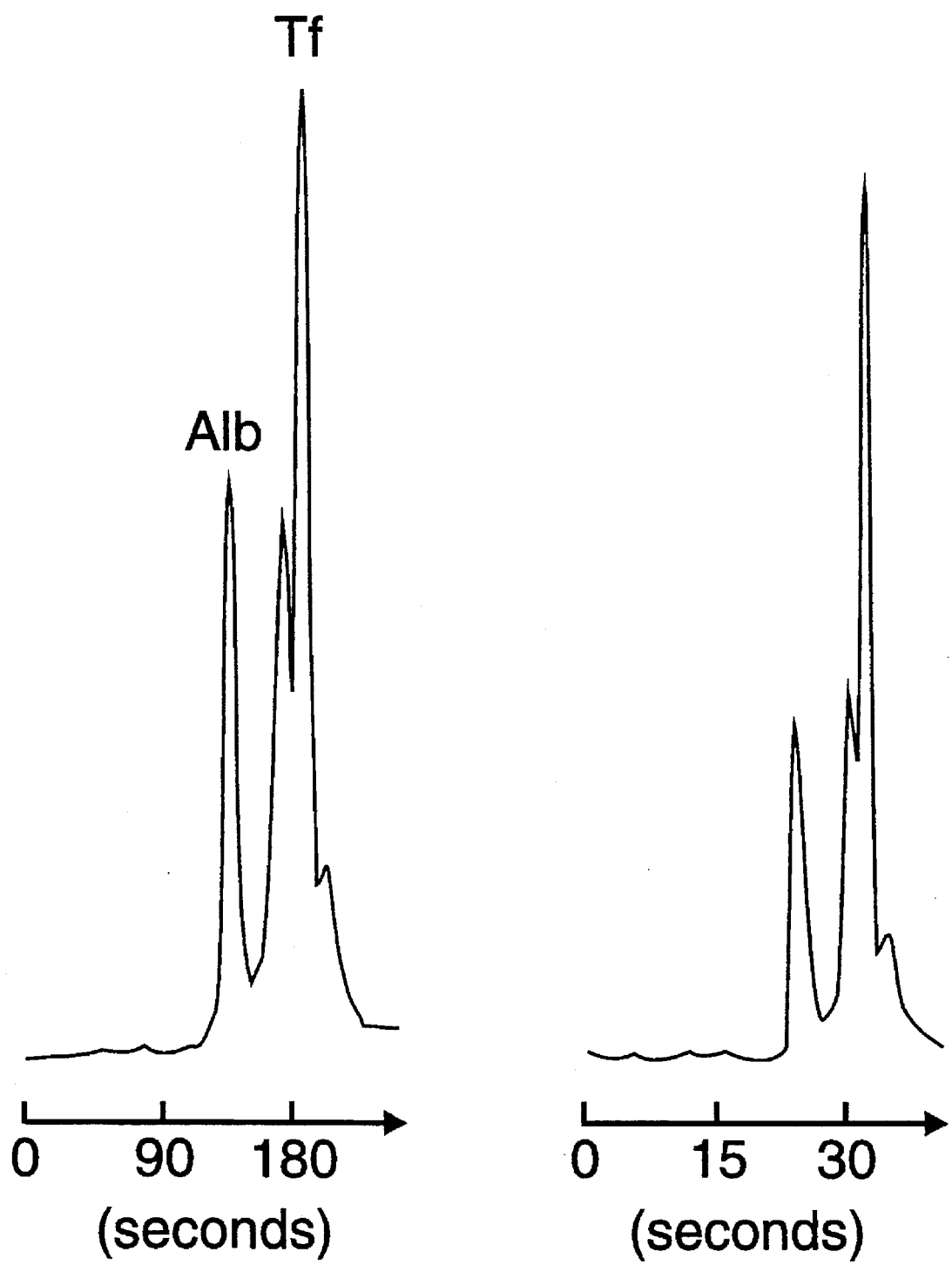
FIGS. 3*a* and 3*b* are detector traces of electrophoretic separations of a mixture of macromolecules at two different voltages, using the same buffer as FIGS. 1*a* and 1*b*.

The polyoxyethylene bis(3-amino-2-hydroxypropyl)/polyoxyethylene his(acetic acid) buffer was then used for separations of proteins to show the efficacy of the buffer on macromolecules. One sample mixture consisted of human serum albumin (Alb) and human transferrin (Tf), each protein dissolved in the buffer to a final concentration of 1.5 and 3.0 mg/mL, respectively. One run, whose electropherogram is shown in FIG. 3a, was performed at 5,000 V (330 V/cm, 0.48 μA), and a second run, whose electropherogram is shown in FIG. 3b, was performed at 30,000 V (2,000 V/cm, 3.5 μA). A comparison of these two electropherograms shows that, like the electropherograms of FIGS. 1a and 1b, the large increase in field strength to 2,000 V/cm does not entail any observable loss of resolution even though the analysis time is considerably shortened, and the peaks remain symmetrical with high resolution.

A second sample mixture of proteins separated in the same buffer solution was one consisting of β-lactoglobulin (L), human transferrin (Tf), equine myoglobin (M) and bovine carbonic anhydrase (CA), with 2 mg of each protein dissolved in 1 mL of the buffer. Again, two runs at different voltages were performed, one at 5,000 V (330 V/cm, 0.45 μA) (FIG. 4a), and the other at 30,000 V (2,000 V/cm, 3.2 μA) (FIG. 4b). Like the comparisons discussed above, no loss of resolution is observed when the high voltage electropherogram is compared to the low voltage electropherogram, and the peaks at both voltages are symmetrical.

B. Diaminopimelic Acid and 2-Amino-2-methyl-1,3-propanediol—FIGS. 5a and 5b

Two separations were performed using a buffer consisting of a mixture of 0.01M diaminopimelic acid and 0.005M 2-amino-2-methyl-1,3-propanediol, pH 8.6. The conductivity of this buffer according to Equation (2) above is $18 \times 10^{-5}$ ohm$^-$cm$^{-1}$. The sample mixture was the same aromatic carboxylic acid mixture listed in the preceding section.

Figures 5A, 5B:
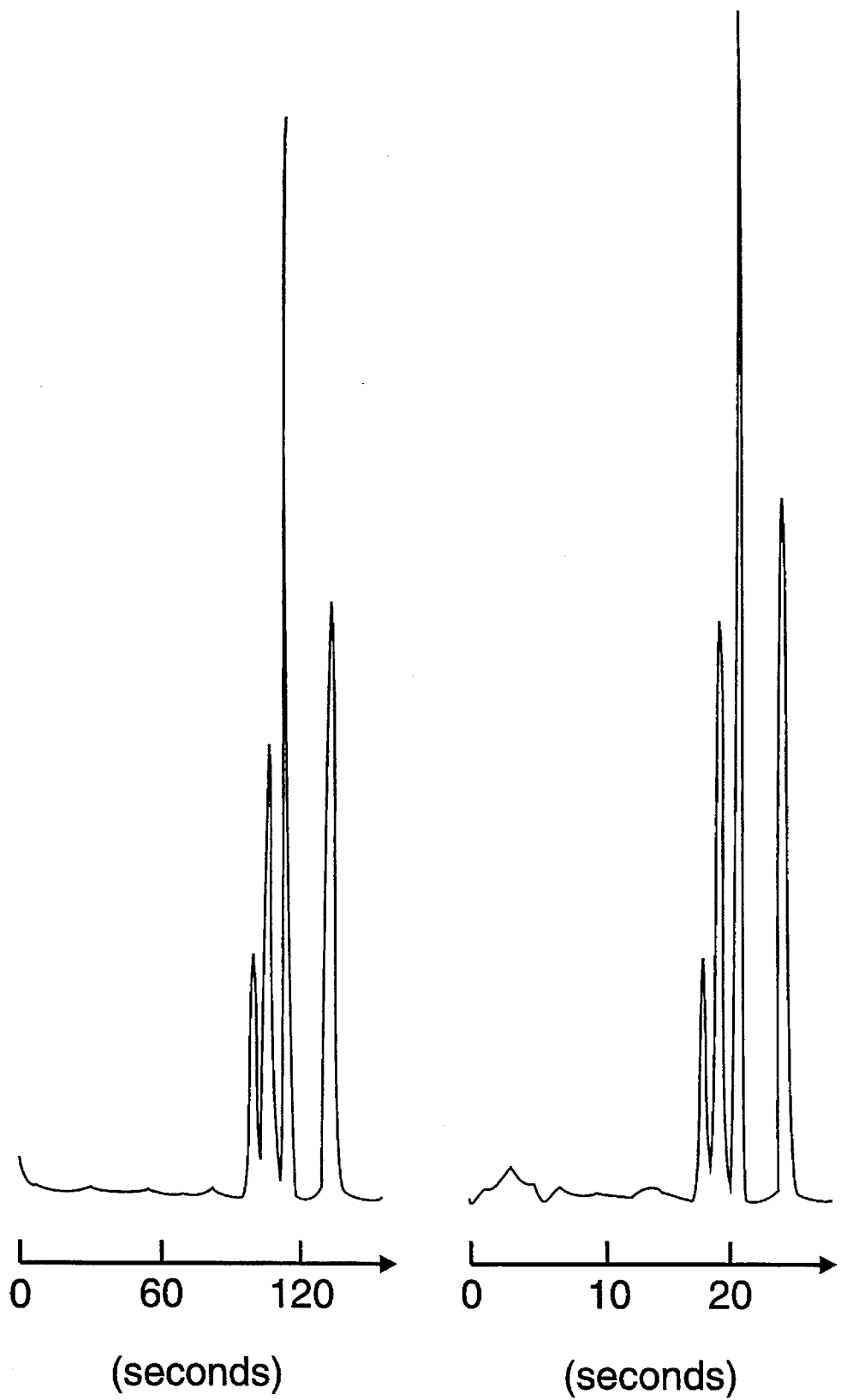
FIGS. 5a and 5b are detector traces of electrophoretic separations of the sample mixture used in FIGS. 1a and 1b at two different voltages, using a mixture of diaminopimelic acid and 2-amino-2-methyl-1,3-propanediol as the buffer.

FIG. 5a is the electropherogram of a run performed at 5,000 V (330 V/cm, 1.2 μA), and FIG. 5b is the electropherogram of a run performed at 30,000 V (2,000 V/cm, 7.5 μA). Once again, the peaks are symmetrical, there is no loss of resolution as the voltage is increased, and the higher field strength is preferable since it shortens the analysis time.

H. Isoelectrically Focused Ampholytes—FIGS. 6a–6d

A buffer was prepared by isoelectrically focusing 40 mL of a 10% (volume/volume) solution of BIO/LYTE 7-9 in the ROTOFOR apparatus, for 12 hours. The resulting pH gradient was divided into twenty fractions with median pH values of 6.72, 6.94, 7.67, 8.03, 8.32, 8.51, 8.69, 8.81, 8.90, 8.98, 9.05, 9.11, 9.16, 9.20, 9.27, 9.34, 9.50, 9.62, 9.77 and 10.10. The pH 8.69 fraction was isolated and diluted 1 part with 39 parts of water. The conductivity of the resulting buffer according to Equation (2) above was $5 \times 10^{-5}$ ohm$^-$ $^1$cm$^{-1}$. For a test sample, the sample mixture of human serum albumin (Alb) and human transferrin (Tf) used in the run represented by FIGS. 3a and 3b was used.

The voltages used and the Figures in which the resulting electropherograms appear are as follows:

Like the results in the section above, these electropherograms show that the resolution with this buffer is independent of the field strength. High field strengths can therefore be used to shorten the analysis time without sacrificing resolution.

III. Low Molecular Weight Ampholytes With pK Close to Isoelectric Point—FIGS. 7a–7d A series of separations were performed using 0.005M lysine, pH 9.6, as a buffer. The conductivity of this buffer according to Equation (2) above was $13 \times 10^{-5}$ ohm$^{-1}$cm$^{-1}$. The detector sensitivity in this case was 0.01 AUFS. The sample consisted of the following proteins dissolved in the buffer:

soybean trypsin inhibitor, 2.5 mg/mL chicken ovalbumin, 3.0 mg/mL conalbumin, 2.5 mg/mL equine myoglobin, 1.0 mg/mL The voltages used and the Figures in which the resulting electropherograms appear are as follows:

Consistent with the other results presented in these Examples, FIGS. 7a through 7d show that the analysis time decreases with field strength, the peaks obtained with this buffer are symmetrical, and the peak resolution is independent of the field strength.

IV. Observations of Resolution vs. Concentration and Conductivity

The buffers used in the preceding sections of these Examples were tested in additional separations of the same solute mixtures, varying the concentrations, and hence the conductivities (as determined by Equation (2) above), of the buffers. The conditions are listed in the following table, which includes the separations reported in the preceding sections of these Examples plus the additional separations. The resolution of the solutes was observed as a function of the buffer concentrations and conductivities. The underlined entries in the table indicate the concentrations and conductivities below which resolution decreased, i.e., these are the lowest concentrations and conductivities where resolution was not dependent on buffer concentration. The improvement of the buffers of the invention over the prior art Tris/HCl buffer is clearly evident, since at a $\kappa$ value of 120 the lower limit for Tris/HCl is at least 6.7 times higher than the lower limit for the other buffers.

VI. UV Spectra of Low Conductivity Buffers—FIG. 9

Figure 9:
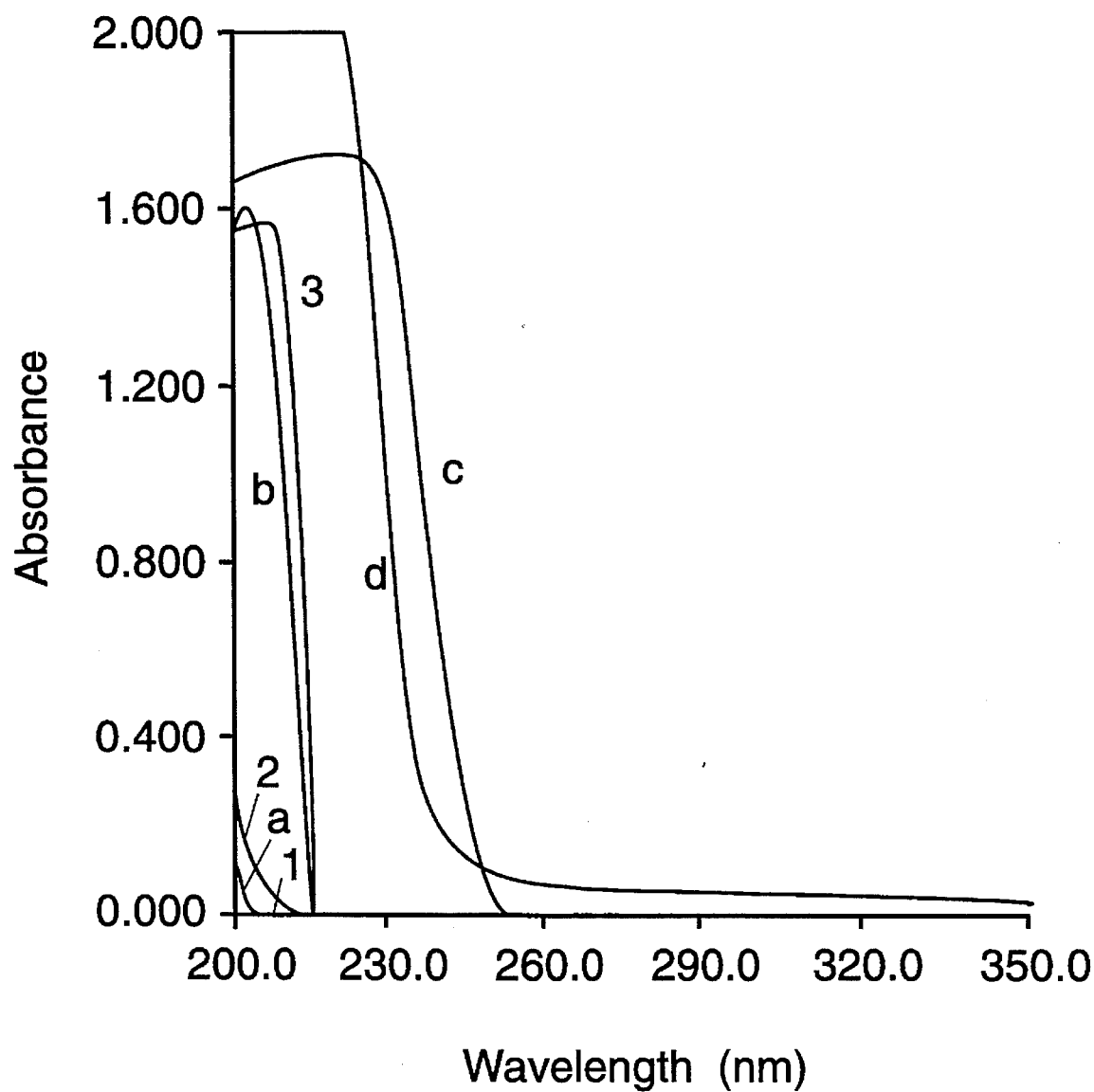
FIG. 9 are ultraviolet absorption spectra of the buffers used in the preceding figures and the prior art buffers.

To determine the optimal ranges for solute detection by light absorptivity for each of the buffers tested above, UV spectra of the buffers were taken together with spectra of prior art buffers. The blank cuvette contained water in each case. FIG. 9 shows these spectra, where:

a: mixture of polyoxyethylene bis(3-amino-2-hydroxypropyl) at 0.3% (weight/volume) and polyoxyethylene bis(acetic acid) at 0.025% (weight/volume), pH 8.6 b: mixture of 0.01M diaminopimelic acid and 0.005M 2-amino-2-methyl-1,3-propanediol, pH 8.6 c: pH 8.69 fraction of isoelectrically focused BIO-LYTE 7–9 d: 0.0005M lysine, pH 9.7

1: 0.05M sodium borate, pH 8.6

2: 0.02M sodium phosphate, pH 6.8

3: 0.05M Tris-acetic acid, pH 8.6

The spectra show that the polyoxyethylene buffers (a) have a very low UV absorption, like the borate (1) and phosphate (2) buffers. The diaminopimelic acid/2-amino-2-methyl-1,3-propanediol buffer (b) has a spectrum resem- Separations Performed at Varying Buffer Concentrations
(Resolution decreases at values below underlined entries)

| Prior Art: Tris/HCl | | | POE amine/ POE acid[a] | | | DAPA/AMPD[b] | | | Isolated Ampholyte[c] Fraction | | | Lysine | | |
|---|---|---|---|---|---|---|---|---|---|---|---|---|---|---|
| conc. M | pH | $\kappa \times 10^5$ ohm$^{-1}$ cm$^{-1}$ | conc. % | pH | $\kappa \times 10^5$ ohm$^{-1}$ cm$^{-1}$ | conc. M | pH | $\kappa \times 10^5$ ohm$^{-1}$ cm$^{-1}$ | conc. % | pH | $\kappa \times 10^5$ ohm$^{-1}$ cm$^{-1}$ | conc. % | pH | $\kappa \times 10^5$ ohm$^{-1}$ cm$^{-1}$ |
| 0.1 | 8.6 | 120.0 | 3.0/0.25 | 8.6 | 55.9 | 0.1/0.05 | 8.6 | 179 | 0.5 | 8.6 | 9.9 | 0.1 | 9.0 | 79 |
| 0.01 | 8.5 | 13.8 | 0.3/0.025 | 8.6 | 6.0 | 0.01/0.005 | 8.6 | 18.0 | 0.25 | 8.6 | 5.0 | 0.01 | 9.6 | 16.8 |
| 0.005 | 8.4 | 7.2 | 0.15/0.0125 | 8.6 | 4.9 | 0.005/0.0025 | 8.6 | 11.5 | 0.05 | 8.6 | 3.2 | 0.005 | 9.6 | 13.0 |
| 0.001 | 8.3 | 4.1 | 0.03/0.0125 | 8.5 | 3.6 | 0.001/0.0005 | 8.6 | 6.8 | 0.025 | 8.6 | 3.0 | 0.001 | 9.5 | 5.7 |

[a] polyoxyethylene bis(3-amino-2-hydroxypropyl) and polyoxyethylene bis(acetic acid)
[b] diaminopimelic acid and 2-amino-2-methyl-1,3-propanediol
[c] BIO-LYTE 7-9

Figure 8:
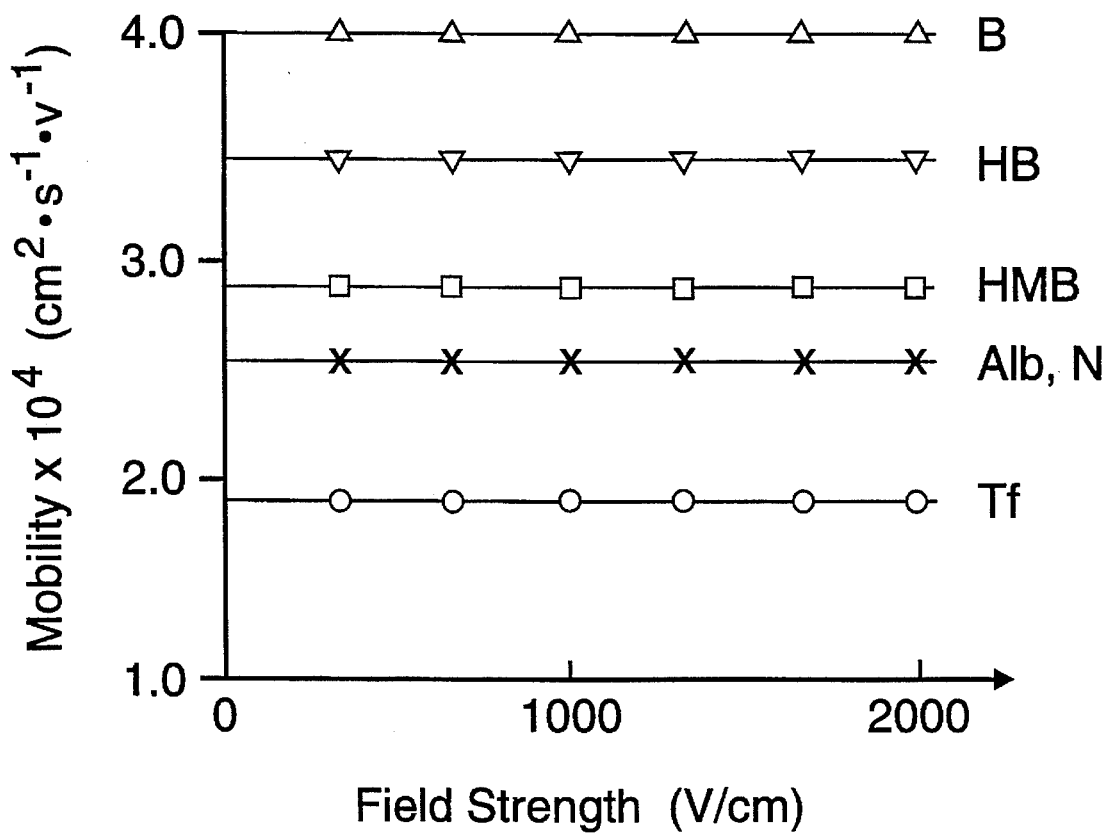
FIG. 8 is a plot of migration velocities of various solutes in the buffer consisting of a mixture of polyoxyethylene bis(3-amino-2-hydroxypropyl) and polyoxyethylene bis(acetic acid), as a function of field strength.

V. Solute Mobility Measurements—FIG. 8

The solutes used in the experiments reported in the preceding sections of these Examples were run in the polyoxyethylene bis(3-amino-2-hydroxypropyl)/polyoxyethylene bis(acetic acid) buffer of Section IA at a series of different field strengths. The migration velocities v of the solutes were measured and translated into mobilities by the following equation:

$$u = v \cdot \frac{L'}{V} \quad (3)$$

where u represents the mobility, L' the length of the capillary, and V the voltage. The mobilities for the four aromatic carboxylic acids (B, HB, HMB and N), human serum albumin (Alb) and human transferrin (Tf) are plotted against the field strength in FIG. 8, which shows that for each solute the mobility is constant and independent of the field strength. This confirms that the Joule heat is negligible and that the conformation of the proteins is not affected by the high field strengths.

bling that of the Tris-acetic acid buffer (3). The absorption of these buffers is negligible at wavelengths above 215 nm. By contrast, the carrier ampholyte buffer (c) and lysine (d) have strong absorptions up to about 250 and 235 nm, respectively. FIGS. 6a–6d and 7a–7d indicate that these buffers can still be used effectively with detection at 210 nm, however.

The foregoing is offered primarily for purposes of illustration. It will be readily apparent to those skilled in the art that the operating conditions, materials, procedural steps and other parameters of the system described herein may be further modified or substituted in various ways without departing from the spirit and scope of the invention.

What is claimed is:

1. A method for electrophoretically separating solutes in a mixture thereof, said method comprising:

(a) injecting an aliquot of said mixture into an electrophoretic separation medium saturated with a buffer solution having a conductivity of less than about $25 \times 10^{-5}$ ohm$^{-1}$cm$^{-1}$;

(b) imposing across said medium a voltage of at least about 300 volts per cm of medium length to cause solutes in said aliquot to migrate electrophoretically along said medium while separating into substantially discrete zones; and (c) detecting said zones as a means of identifying said solutes.

2. A method in accordance with claim 1 in which said voltage is at least about 600 volts per cm.

3. A method in accordance with claim 1 in which said voltage is at least about 750 volts per cm.

4. A method in accordance with claim 1 in which said voltage is at least about 2,000 volts per cm.

5. A method in accordance with claim 1 in which said buffer solution has a conductivity of from about $1\times10^{-5}$ ohm$^{-1}$cm$^{-1}$ to about $20\times10^{-5}$ ohm$^{-1}$cm$^{-1}$.

6. A method in accordance with claim 1 in which said buffer solution has a conductivity of from about $2\times10^{-5}$ ohm$^{-1}$cm$^{-1}$ to about $10\times10^{-5}$ ohm$^{-1}$cm$^{-1}$.

7. A method in accordance with claim 1 in which said voltage is from about 1,000 to about 5,000 volts per cm and said buffer solution has a conductivity of from about $2\times10^{-5}$ ohm$^{-1}$cm$^{-1}$ to about $10\times10^{-5}$ ohm$^{-1}$cm$^{-1}$.

8. A method in accordance with claim 1 in which (a) comprises injecting said aliquot into a capillary column filled with said buffer solution; and (b) comprises imposing across said capillary column a voltage of at least about 600 volts per cm.

9. A method in accordance with claim 1 in which said buffer solution is a solution of a member selected from the group consisting of:

(i) a buffering agent having a molecular weight of at least about 100 and from one to four charged buffering groups per molecule, (ii) a carder ampholyte fraction having a pH range of about 0.2 or less obtained by recovering a fraction from a carder ampholyte equilibrated by isoelectric focusing, (iii) a low molecular weight buffering ampholyte defined as a buffering ampholyte having a molecular weight of about 1,000 or less and an isoelectric point, said buffering ampholyte being equilibrated to said isoelectric point and further having three or more pK values, at least one of which is within about 1.0 of said isoelectric point, and (iv) a high molecular weight buffering ampholyte defined as a buffering ampholyte having a molecular weight of at least about 2,500 and derivatized to contain one acidic group and one basic group, said acidic and basic groups having substantially equal pK values.

10. A method in accordance with claim 1 in which said buffer solution is a solution of a buffering agent having a molecular weight of at least about 100 and from one to four charged buffering groups per molecule.

11. A method in accordance with claim 10 in which said buffering agent is a mixture of diaminopimelic acid and 2-amino-2-methyl-1,3-propanediol.

12. A method in accordance with claim 1 in which said buffer solution is a solution of a soluble inert polymer having a molecular weight of at least about 2,000 and from one to four charged buffering groups per molecule.

13. A method in accordance with claim 12 in which said soluble inert polymer is a derivatized polyoxyethylene having a molecular weight of from about 2,500 to about 5,000 and from one to three charged buffering groups per molecule.

14. A method in accordance with claim 12 in which said soluble inert polymer is a derivatized polyoxyethylene having a molecular weight of from about 2,500 to about 5,000 and two charged buffering groups per molecule.

15. A method in accordance with claim 12 in which said soluble inert polymer is a mixture of first and second derivatized polyoxyethylenes, each having a molecular weight of from about 2,500 to about 5,000, said first derivatized polyoxyethylene containing two acidic buffering groups and said second derivatized polyoxyethylene containing two basic buffering groups.

16. A method in accordance with claim 12 in which said soluble inert polymer is a mixture of polyoxyethylene bis(3-amino-2-hydroxypropyl) and polyoxyethylene bis(acetic acid), each having molecular weights of approximately 3,000 to 3,500.

17. A method in accordance with claim 1 in which said buffer solution is a solution of a carder ampholyte fraction having a pH range of about 0.2 or less obtained by recovering a fraction from a carder ampholyte equilibrated by isoelectric focusing.

18. A method in accordance with claim 17 in which said carrier ampholyte fraction has a pH range of about 0.1 or less and a midpoint within the range of about pH 3 to about pH 10.

19. A method in accordance with claim 17 in which said carrier ampholyte fraction has a pH range of about 0.1 or less and a midpoint within the range of about pH 5 to about pH 9.

20. A method in accordance with claim 1 in which said buffer solution is a solution of a low molecular weight buffering ampholyte defined as a buffering ampholyte having a molecular weight of about 1,000 or less and an isoelectric point, said buffering ampholyte being equilibrated to said isoelectric point and further having three or more pK values, at least one of which is within about 1.0 of said isoelectric point.

21. A method in accordance with claim 20 in which at least two of said three or more pK values differ from each other by at least about 3.0.

22. A method in accordance with claim 20 in which said buffering ampholyte is a member selected from the group consisting of lysine, aspartyl-aspartic acid, glycyl-L-histidine, glycyl-aspartic acid, hydroxylysine, glycyl-glycyl-L-histidine, N-cyclohexyliminodiacetic acid, and cyclobutane-1,2-bis(N-iminodiacetic acid).

23. A method in accordance with claim 20 in which said buffering ampholyte is lysine.

24. A method in accordance with claim 1 in which said buffer solution is a solution of a high molecular weight buffering ampholyte defined as a buffering ampholyte having a molecular weight of at least about 2,500 and derivatized to contain one acidic group and one basic group, said acidic and basic groups having substantially equal pK values.

25. A method in accordance with claim 24 in which said buffering ampholyte is a derivatized polyoxyethylene glycol with an acid moiety at one end and a basic moiety at the other.

26. A method in accordance with claim 24 in which said buffering ampholyte is a derivatized polyoxyethylene glycol with a boric acid moiety at one end and an amine moiety at the other.

\* \* \* \* \*